United States Patent [19]

White

[11] Patent Number: 5,912,412
[45] Date of Patent: Jun. 15, 1999

[54] **VARIETIES OF *POA ANNUA***

[75] Inventor: Donald B. White, White Bear Lake, Minn.

[73] Assignee: Regents of University of Minnesota, Minneapolis, Minn.

[21] Appl. No.: 08/711,913

[22] Filed: Sep. 12, 1996

[51] Int. Cl.$^6$ .............................. A01H 5/00; A01H 5/10
[52] U.S. Cl. ............................................ 800/200; 800/298
[58] Field of Search ........................... 800/200, DIG. 55, 800/235, 250; 47/58, DIG. 1; Plt./90.2

[56] References Cited

PUBLICATIONS

Bridget Anne Ruemmele, *Reproductive Biology in Poa Annua L.*, A Thesis Submitted to the Faculty of the Graduate School of the University of Minnesota, 1989, (148 pages).

Paul Grumstrup Johnson, *Genetics and Physiology of Flowering in Selected Poa Annua L.*, A Thesis Submitted to the Faculty of the Graduate School of the University of Minnesota, Jun., 1995, (122 pages).

P. G. Johnson, et al., *Application of mist controlled pollen shed with an excised stem technique in Poa annua breeding*, abstract from the Annual Meeting of the Crop Science Society of America, Oct./Nov., 1990.

P. G. Johnson, et al., *Inheritance of Flowering Requirements in Poa annua L.*, abstract from the Annual Meeting of the Crop Science Society of America, Oct./Nov., 1992.

P. G. Johnson, et al., *Requirements for Flower Induction in Poa annua L.*, abstract from the Annual Meeting of the Crop Science Society of America, Oct./Nov., 1993.

P. G. Johnson, et al., *Inheritance of Flowering Pattern in Poa annua reptans (Hausskn. and Poa annua annua (L.).*, abstract from the Annual Meeting of the Crop Science Society of America, Oct./Nov., 1994.

P. G. Johnson, et al., *Implications of flowering pattern to growth and the culture of annual bluegrass (Poa annuaL.)*, abstract from the Annual Meeting of the Crop Science Society of America, Oct./Nov., 1995.

H. H. Kearwer, et al., *Poa annua L.–Agrostis stolonifera L. Competition Under Putting Green Conditions*, abstract from the Annual Meeting of the Crop Science Society of America, Oct./Nov.,1989.

V. W. Cline, et al., *Annual Bluegrass (Poa annua L.) –Creeping Bentgrass (Agrostis palustris HUDS.) Seasonal Population Fluctuations on Golf Greens in Minnesota.*, abstract from the Annual Meeting of the Crop Science Society of America, Oct./Nov., 1992.

V. W. Cline, et al., *Seasonal Changes in Annual Bluegrass (Poa annua L.) Morphology of Golf Greens in Minnesota.* abstract form the Annual Meeting of the Crop Science Society of America, Oct./Nov., 1992.

P. H. Velguth, et al., *Ploidy Level Variation in Breeding Materials of Poa annua L. (Annual Bluegrass)*, abstract from the Annual Meeting of the Crop Science Society of America, Oct./Nov., 1992.

P. H. Velguth, et al., *The Relative Frequency of Diploid and Tretraploid Poa annua L. on Selected Golf Courses in Minnesota.*, abstract form the Annual Meeting of the Crop Science Society of America, 1993.

Canaway et al. Ball roll characteristics of five turfgrasses used for golf and bowling greens. J. Sports Turf Res. Inst. vol. 68, pp. 88–94, 1992.

Danneberger et al. Annual bluegrass seedhead emergence as predicted by degree–day accumulation. Agron. J. vol. 76, pp. 756–758, 1984.

Johnson, P.G. Genetics and Physiology of Flowering in Selected *Poa annua L.* (Golf Course Turf). Dissertation Abstracts International. vol. 56, No. 7b, p. 3528, 1995.

*Primary Examiner*—Douglas W. Robinson
*Assistant Examiner*—Melissa L. Kimball
*Attorney, Agent, or Firm*—Merchant, Gould, Smith, Edell, Welter & Schmidt, PA

[57] ABSTRACT

Novel varieties of *Poa annua* that are perennial and have characteristics desired for a turfgrass, including dark green color, vigor, disease resistance, and restricted flowering.

41 Claims, No Drawings

VARIETIES OF *POA ANNUA*

FIELD OF THE INVENTION

This invention relates to development of cultivated varieties from wild populations of one of the most widespread weeds in the world, *Poa annua*, and, in the process, domesticating the species and elucidating genetic information and inheritance of major characteristics related to flowering, perenniality, and cytology and the generation of cultivated varieties for sports turf, including golf turf applications.

BACKGROUND OF THE INVENTION

Annual bluegrass (*Poa annua L.*) is found on every continent and is recognized as one of the five most widespread weeds of the world. It is the only grass listed in the top five weeds. The great genetic variation in the species enables broad adaptability to a wide range of habitats. The species is most often found on sports turf fields, including golf fields. However, grounds keepers for most sports fields consider *Poa annua* as a pernicious and invasive weed because of variability in plant type and susceptibility to diseases, stress, and damage. They typically mount programs to eradicate it or at least discourage its growth. Sport turfgrass managers typically consider *Poa annua* a weed because of its characteristic light color, its profuse, year-round flowering habit, and its susceptibility to factors including heat, drought, disease, and low temperature. These criticisms are most valid in areas with high summer temperatures where *Poa annua* behaves as a true annual. However, the sport groundskeeper also must contend with semi-perennial types of *Poa annua* which prosper under conditions of moist soil, cool temperate climate, high levels of soil nutrients, and frequent close mowing. Under such conditions, the groundskeeper is up against a nemesis that propagates extensively and maintains a prolific seed bank. In addition, wild biotypes are very susceptible to many fungal diseases.

There is a considerable industry focused on the control, suppression, and eradication of *Poa annua* on golf courses, in sod fields, and at times on athletic fields and lawns. At least 16 states list it as a noxious weed. As a result of this listing, grass seed contaminated with the seed of *Poa annua* cannot be sold in many states.

There are several reasons why *Poa annua* as a species is considered a weed. It is often described as flowering profusely and continuously throughout the growing season. This is in part because many ecotypes of *Poa annua* do not exhibit day length or vernalization requirements for flowering. An additional shortcoming of the wild biotypes is that the annual type is particularly susceptible to freeze damage when its crowns are hydrated. Not only is the wild-type *Poa annua* intolerant of wet freezing conditions, but it is also very susceptible to damage by heat and drought stress.

The wild ecotypes possess characteristics that make a plant noxious and weed-like. However, in the right combination, some of these characteristics can be beneficial for producing a desirable variant. *Poa annua* is present in variable populations with a nearly endless array of genotypes ranging from annual to perennial. Hence, there is a wide genetic base of materials from which desirable cultivars may be produced. In addition, the species, as a whole, is tolerant of shade and poorly aerated soil conditions, including compaction and excessive water. Most of the wild types exhibit no seed dormancy or after ripening requirements, so seed is readily available to produce new plants. In addition, *Poa annua* seeds are known to remain viable for many years.

A botanical variety, *Poa annua reptans*, is a perennial often having a spreading habit with the potential for developing cultivars that would produce a uniform dense perennial turf. It is generally stoloniferous and propagates in the field by rooting at nodes on stolons, as well as by seed. Many of its characteristics are complementary to those of the annual variety of *Poa annua*. For example, *Poa annua reptans* can exhibit either daylength or vernalization (cold treatment) or both requirements for flowering. *Poa annua reptans* can exhibit seed dormancy or after ripening. However, many *Poa annua reptans* can tolerate heat, drought, shade, and low aeration (excessive moisture or compaction), ⅛" height of cut, and possess other desirable traits.

Some individual biotypes of *Poa annua* possess desirable turfgrass characteristics for golfing applications. As an unwanted invader of bentgrass greens, *Poa annua* can, under certain conditions, be cultivated and bred to produce an acceptable turf and putting surface. However, the broad expression of phenotypic variation in color, growth rate, habit of growth, flowering habit, and susceptibility to disease and stress damage make *Poa annua* undesirable despite its tolerance of low (⅛) height of cut and poor soil conditions.

*Poa annua* can seed prodigiously and injured areas can eventually recover from seed. On these bases, *Poa annua* is unreliable and is despised by turf managers because it often fails suddenly at critical times during the growing season. Typically, this failure results from high susceptibility to disease and low heat or cold tolerance and the normal completion of the annual growth cycle.

Cultivars of *Poa annua*, particularly of perennial types, with desired restricted flowering habit, have not been previously available.

Hence, there is a need for uniform, reliable variety of *Poa annua* with characteristics of a desirable turfgrass for sports fields, particularly golf courses. There is a need for a *Poa annua* variety and seed that provides a uniform population with desirable traits, that is a dense turf having a uniform, dark green color, restricted flowering habit, and good performance at moderate to low fertility. Such varieties of *Poa annua* will also have characteristics that will enable them to tolerate the low mowing, disease exposure, and traffic conditions of a golf course or other sporting field.

SUMMARY OF THE INVENTION

New cultivars of *Poa annua* have now been produced having desirable turfgrass characteristics. These new cultivars include breeding selections designated MN184, MN208, MN42, MN117 and MN234.

The new *Poa annua* cultivars of this invention are uniform, resistant to disease, hardy under conditions of drought and temperature extremes, have superior dark green color, density and spreading vigor, fine texture and uniformity, good seed production, restricted flowering habit, and respond to mowing with increased density. These characteristics provide a hardy, healthy, and desirable *Poa annua* for golf turf use.

In particular these cultivars include perennial varieties of *Poa annua*. More particularly the perennial varieties of *Poa annua* include perennial varieties of *Poa annua reptans*. These perennial varieties have desirable characteristics not commonly found in wild-type *Poa annua*.

Advantageously, the variety may have a restrictive flowering habit. Advantageous flowering habits include reduced flowering, e.g., flowering predominantly in the spring, or where continuous, having reduced flowering in summer and fall. In one embodiment the restrictive flowering habit includes flowering predominantly in mid-spring for about 2–3 weeks or for about 4–6 weeks. In another embodiment, the restrictive flowering habit includes at least two flushes of flowers, which can occur in mid-spring separated by about 3–5 weeks, with potentially a third flush in the fall. The restrictive flowering habit can also include producing secondary flowering tillers.

Flowering can be induced by one or more conditions typical of varieties of *Poa annua*. Advantageously, the perennial variety of *Poa annua* has flowering induced by a condition selected from the group consisting of vernalization (exposure to cold), short day length, or long day length. Vernalization or exposure to cold, as used herein, encompasses the important features of vernalization with respect to flower induction. A variety can exhibit flowering that is unaffected by day length. In addition, a variety can exhibit a faculative vernalization, that is, flowering induced by any one of cold exposure, short day length, or long day length.

The flowering of a *Poa annua* variety of the invention can also be characterized by the quantity and growth habit of the flowers and flower stalks. In one embodiment, when grown for seed, the variety produces an unusually high number of flower stalks per plant.

The quantity and quality of seed production can differ from variety to variety. For at least one variety, more seed is produced if the plants are subjected to cold.

The variety of *Poa annua* can also have a characteristic growth habit. Advantageously, the growth habit allows mowing to about ⅛". In one embodiment, in the unmowed state, the growth habit includes a vigorous, low, and dense spreading growth habit. The growth habit can also include, in the unmowed state, low spreading stolons with multiple tillers per stolon during flower production. In another embodiment, the growth habit can include, in the unmowed state, a tightly packed, upright, but still spreading mound. Another growth habit includes, in the unmowed state, a dense but decumbent growth. Alternatively, the growth habit can include, in the unmowed state a tightly packed, dense, spreading mound. One variety has a characteristic growth habit that includes, in the unmowed state, a tightly packed, dense, spreading mound, which when left unmowed takes on a conical shape.

The perennial varieties of *Poa annua* include cultivated *Poa annua* varieties selected from the group including or consisting of MN184, MN117, MN208, MN234, and MN42. Varieties of the invention also include a *Poa annua* variety having all of the physiological and morphological characteristics of any of the *Poa annua* varieties MN184, MN117, MN208, MN234, or MN42.

Additional embodiments of the invention include plant parts such as seed produced by, an ovule of, an isolated plant of, and plant tissue derived from the perennial varieties of *Poa annua*, including the varieties selected from the group including or consisting of varieties designated MN184, MN117, MN208, MN234, and MN42.

The varieties of the invention can be reproduced by any of several methods, for example, from seed or vegetatively. The invention includes perennial varieties derived from varieties of the invention.

Varieties of the invention can be produced from seed. The invention includes seed producing a *Poa annua* variety selected from the group including or consisting of MN184, MN117, MN208, MN234, and MN42. Such seed includes seed that has been accorded American Type Culture Collection (ATCC) Accession Nos. selected from the group consisting of 97711, 97713, 97714, 97715, and 97712, deposited on Sep. 12, 1996 at the American Culture Collection (12301 Parklawn Drive, Rockville, Md., 20852).

Varieties of the invention include a variety that withstands mowing to about ⅛", that flowers after vernalization for about 3 weeks or less, and that produces, when grown in a pot, a dense mound of finely textured plant material.

DETAILED DESCRIPTION OF THE PREFERRED EMBODIMENTS

*Poa annua* is used to describe a widely variable species of grass. *Poa annua reptans* is used to describe perennial biotypes. New, useful cultivars of *Poa annua reptans* have now been selected for and bred with desirable characteristics that come true from seed. The new cultivars have specific features for use as turfgrasses for golf turf, without the troublesome characteristics of the wild-type *Poa annua* weed.

The novel varieties of the present invention were derived from seed collected from annual bluegrass plants that appeared more desirable than the general populations. Seed was individually collected from multiple plants and from multiple locations across the United States.

Upon receipt, seed was accessioned with a given family number, and a small number of seed from each family was germinated in 2"–6" greenhouse pots, in a standard potting mix of peat, sand and soil, and grown under standard greenhouse culture. From each family, at least fifteen seedlings were produced. Individual seedlings of each family were assigned a letter designation (A–O) to accompany the family number.

The most desirable plant in each family was identified and selected for further growth and selection. Plants were propagated from seeds or vegetatively (via stolons) through successive generations, selecting from each seeded generation for plants exhibiting superior vigor, health, dark green color, restricted flowering habit, dense growth habit, short stolons, and performance at low fertility. The most desirable plants from each generation were selected and grown through successive generations.

Breeding

*Poa annua* varieties and crosses have been bred to at least seven generations using two basic techniques. The first technique is a combination of the excised stem and mist techniques. A refinement of the excised stem technique has also been used.

The fog or mist technique (developed by Burton and others) enables control of pollen shed and easy emasculation. In combination with the excised stem technique, anthers are expressed in a manner such that they are very accessible for emasculation, while at the same time the mist inhibits pollen shed. This combined technique permits controlled pollination with *Poa annua*, which had been problematic by other methods.

The combined excised stem-mist technique was carried out as follows: A Plexiglas box was constructed and interfaced with an ultra-sonic humidifier with mist control and a timer. It was determined that 15 days is the optimum length of time to leave excised stems in the nutrient solution after pollination for the best seed numbers and quality. Tight control over the mist is especially essential with *Poa annua*. A lapse of as little as 15 minutes when the anthers are being exerted can result in pollen shed and loss of control of the pollination. Under the constraints, continuous control of the misting operation is essential. At the same time, constant (24 hours) mist inhibited flower opening and substantially reduced seed-set. It was determined that the mist had to be constant only during the normal time when pollen was shed (1 a.m. to 9 a.m.) to control the pollination process. Allowing the flowers to dry out in between times proved to be beneficial resulting in improved seed set.

It was determined that the optimum sugar concentration for producing seed from excised stems of *Poa annua* was in the range of between 4 and 10 percent. Fructose was better than sucrose as a carbon source and supplemental light was important at low sugar levels. In these studies, the greatest production of seeds by weight and number occurred when stems were maintained in the sugar solution for 15 days. Maximal seed levels were obtained when excision occurred one day prior to anthesis. Better results were obtained with intermittent mist application compared to continuous mist exposure.

In addition, the density of the source plants influence the floret number. Higher plant density was typically associated with lower numbers of florets.

Selection Criteria

The initial collections of *Poa annua* and subsequent generations were selected for a number of characteristics desired in a turfgrass. These characteristics include perennial nature, dark green color, density, ruggedness, spreading vigor, fine to medium texture, uniformity, cold tolerance, seed dormancy period, seed production, photoperiod, vernalization, restricted flowering habit, and ploidy.

Numerous superior individual *Poa annua* types were identified through selection, and developed through the Pedigree Breeding method. Selection involved the following steps:

1. Collecting first generation seed;
2. Obtaining and evaluating progeny from the first generation seed, and selecting progeny meeting selection criteria;
3. Obtaining second generation seed;
4. Obtaining and evaluating second generation progeny and selecting those progeny meeting selection criteria;
5. Estimating the degree of cross-pollination within the second generation; and
6. Evaluating the new population of progeny for occurrence of the desired trait.

Perennial Nature

An important criteria for nearly all golf turf conditions is that the grass must be perennial in nature. There are a few applications in which an annual variety could possibly be of use, but in most applications for golf and other sport turfs, a perennial is required.

Perennial biotypes of *Poa annua* produce stolons. Stolons are elongated, above the soil, horizontal stems (vegetative shoots) that emanate from a crown and produce buds, nodal and internodal structures. Normally, adventitious rooting may take place at the nodes and associated buds under supportive growing conditions.

Disease Resistance

Disease resistance is also an important trait for application in golf and other sport turfs. A plant that is disease resistant is defined as showing general good health and resistance to diseases common to turfgrasses. These diseases include "Dollar Spot" (*Sclerotinea homeocarpa*), and fusariums which are two of the most common diseases on golf courses. *Poa annua* that show less susceptibility to disease than the wild type are preferred. The preferred types exhibit greater tolerance or greater resistance to disease than wild biotypes.

Typically, to determine disease resistance, a *Poa annua* cultivar is propagated until there is sufficient material for a field planting. Then a field planting is made, typically in a field in which the disease is known to be present. The plants are observed and compared with wild type controls. This can be done using hundreds of types and only a small percentage will be classified as disease resistant. Disease resistance is generally determined by a lack of disease symptoms. Each disease is expressed in the plants by typical symptoms which include lesions, less vigorous growth, loss of color, and finally leaf senescence and death to the plant.

Mowing

An important selection criterion for grass desired for use on a golf course or other sport field is that it must tolerate mowing practices appropriate for such sport fields or golf greens. For example, turf on a golf green is typically mowed to a height of only about ⅛". In other golf course applications, a grass must tolerate mowing to about ½". Selection for mowing involves mowing to the desired height and selecting the surviving plants.

The ability to survive close mowing relates to the habit of growth of the grass. The stolon of the preferred plants has a horizontal habit of growth such that it produces new growth below the desired mowing height (short stolons). The meristems must be maintained below the mowing height, but above the ground. The selections have meristems below ⅛". Selections have a stolon with a horizontal habit of growth such that they produce increased or maintained density when mowed at that height.

Under mowed conditions of ⅛" to ¼", each of the cultivars MN 184, MN 42, MN 208, MN 234 and MN 117 are medium textured. In addition, the grass must mow "cleanly", to minimize damage, promote healing, and present a smooth surface.

Density

A uniformly dense turf is important both for aesthetic and functional considerations in golf and other sport turf applications. Density includes the number of leaves per unit area and the habit of growth of the leaves. For example, the leaves are preferably both tightly packed and upright. For golf greens and fairways, the density is sufficient to cushion and support a golf ball. On a golf green, the density is sufficient to support a golf ball such that it rolls truly.

Density is directly related to leaf texture and number per unit area. A perennial *Poa annua* turfgrass for golf and other sporting applications preferably has a fine to medium textured leaf. The leaf is preferably stiff as well.

Color

A dark green turfgrass is the aesthetic preference for most applications in golf and sport turfs. In addition, the color is also related to the chlorophyll content.

Flowering Habit

Wild type *Poa annua* flower continuously during the spring, cool parts of the summer, and the fall. For sport turf applications, particularly for golf and golf greens, a restrictive or reduced flowering is advantageous. Restrictive flowering is defined herein to mean less than the continuous flowering habit of the wild type. For example, flowering for only several weeks in the spring is desirable. Another desirable flowering trait is that the flowering is not as prolific as in the wild type, generally about 50% of that found in the wild type is desirable, so that the density of flowers in the turf is decreased.

Continuous flowering is defined herein as flowering not only in the Spring, but continuing to flower throughout the remainder of the growing season (Spring, Summer and Fall).

Seasonal flowering is defined herein as flowering only in the Spring, generally after exposure to cold, or inductive day length and exhibiting little or no flowering during the remainder of the growing season.

Vernalization

Vernalization is defined herein as exposure of plants to cool temperatures (below about 40° F.) which results in flower initiation.

Facultative vernalization is defined as inductive short day length or long day length substituted for vernalization (exposure to cold).

The inventive cultivars require vernalization or inductive day length for flower production.

Hardiness

A turfgrass for a sporting application must be sufficiently hardy to survive under the conditions in which it will be grown and used. These conditions relate to prevailing use, mechanical wear to which the turf will be subjected, and the environmental (climactic) conditions. For example, a turfgrass that will survive year-round out of doors in Minnesota can be considered sufficiently hardy to survive winter in the continental United States.

Habit of Growth

The habit of growth of a *Poa annua* varies according to whether the plant is annual or perennial, and if it exhibits a seasonal or continuous flowering habit.

The annual types have no vernalization or day length requirements to flower. They exhibit a bunch type growth habit, and flower throughout the growing season. In the perennial types, habit of growth varies according to flower induction requirements. Generally, all of the perennial types exhibit some environmental induction period before flowering is initiated.

Prior to flower induction, most perennials exhibit a close, dense, spreading mound of leaf structures with little vertical growth. After flower induction, under unmowed conditions, the habit becomes more open as culms (flowering stems of grass) elongate. The plants exhibit typical mature grass characteristics of elongated culms topped by a typical panicle form of inflorescence.

Seed

A desirable turfgrass for golf or other sporting or commercial applications must produce sufficient seed to support commercial production. In addition, it is desirable that the seed can be harvested by standard commercial or other uncomplicated methods. Disease can be a problem in a seed production field. It is important that the *Poa annua* variety resist diseases present in the seed field. Plants in seed fields can be susceptible to the same diseases as other stands of *Poa annua*, and in addition they can be susceptible to rust and mildew. Mildew resistance is a particularly desirable trait.

To allow mechanical harvesting by standard methods, the seed stock preferably exhibits a vertical growth habit. When in the seed field, the grass is grown to a total height of 10" or more. Preferably, the seed stock and flower of the grass should be about 12–14" from the surface of the soil.

Variation (Uniformity)

Uniformity of a *Poa annua* turfgrass is described relative to that fraction of the turf that does not include one or more of the desired selection characteristics. Uniformity is also called homogeneity. Typically for golf or sporting applications, less than about 10% of the seed or plants can be variant from type.

Specific, novel varieties of *Poa annua* have been selected and propagated true both vegetatively (stolons) and from seed. These varieties include those designated MN184, MN42, MN208, MN234, and MN117. Each novel variety has been selected using the above-described criteria.

MN184

MN184 was derived from family 16 from seed originally collected from a plant on a golf course on Long Island, N.Y. Seedlings of this family exhibited above average vigor, definite seasonal flowering, developed extremely dense turf and produced large numbers of short stolons. Verdure was fine to medium textured, dark green in color, and plants spread slowly, mowed cleanly, and performed well under low fertility in the greenhouse. Seedlings derived from plant 16B were darkest green in color than others in the family; 16A and 16C were also fine textured, dark and slow spreading.

A 16B plant was selected from the $F_2$ generation for further development. Plants derived from the 16B plant showed side tillering off main shoots and developed seed heads 4–5 inches taller than the verdure (total height about 12+ inches), which can enhance seed harvest. Plants generated from seed were very uniform, exhibiting strong maternal inheritance. Trueness to type was observed in each succeeding generation.

The 16B selection was re-accessioned as MN184. This variety was propagated asexually (via stolons). Stolons were collected from clonally propagated plants, exposed to a cold treatment in a 38° F. cooler, and subsequently placed in a greenhouse medium until well rooted. The plants were then planted in an experimental nursery seed trial in Tangent, Oreg. The field was previously treated with an herbicide to eliminate the possibility of weeds or wild types. The rooted stolons were planted on a 12"×12" spacing into activated charcoal treated spots and maintained for initial seed increase. (The charcoal inactivated the herbicide.) Seed harvested from these plots was used to establish small nursery plots at the Pickseed West trial farm. The seed from this clonal planting was used to establish current nurseries. The seed from the current nurseries was used to establish a one acre seed nursery at a remote site in the Willamette Valley. Each successive planting was evaluated for trueness to type and maintained under close supervision.

MN184 requires vernalization (cold treatment) for flowering. It is unaffected by day length and exhibits a strongly seasonal flowering habit, producing flowers for only a short time in the Spring. Thus, from mid-summer (after seed-maturity) until vernalization, the plants develop only vegetative structures and typical dense habit. This variety forms a dense, slowly spreading mound under non-mowed conditions, opening up after flower induction during elongation of flowering culms. Under mowed conditions, it maintains a dark green verdure with unobtrusive flowers that are normally mowed off at putting green height. It exhibits resistance to snow mold, dollar spot, mildew, and rust under field conditions.

MN42

MN42 was derived from seed collected from a chance seedling on the practice green at the Nassau Country Club, (Nassau, N.Y.). The seed was accessioned as family 3. Fifteen plants were started in seed pots and evaluated for desired characteristics.

Plants in this family exhibited a vigorous growth habit, dark green color, fine texture, low spreading growth habit and production of multiple tillers per stolon during flower production. Progeny come true to type, with strong expression of maternal inheritance. Early observations of this family of seedlings showed above average vigor, a range of flowering habits, above average density, stoloniferous habit, fine texture, and above average color. Specific selections were made for dark green color and compact growth habit. Specifically, plant 3A was identified as a superior plant in the family, and was continued.

3A was reaccessioned as MN42, and was noted to have a more vigorous spreading habit than observed in other families. The variety has consistent features of dark color, fine texture, low, spreading stolons with good vigor. Successive generations of MN42 have been produced from seed and also maintained vegetatively.

MN42 was propagated asexually (by stolons) and planted in an experimental replicated nursery in Tangent, Oreg., as described above for MN184. Seed harvested from these plots was used to establish small nursery plots and to establish the current nurseries, as described for MN184. Nursery seed was used to establish a 1 acre seed nursery at a remote site in the Willamette Valley.

Each successive planting was evaluated for trueness to type and maintained under close supervision. MN42 has remained stable. It is a dark green, moderately vigorous, perennial with a dense spreading flat mound which regularly develops multiple (up to 5) secondary flowering tillers during the flower development period. It also differs in that it has a seasonal flowering habit with a longer period of flower production over the season than MN184, and exhibits facultative vernalization in that flowering is induced by either cold treatment or short days. Although no cold treatment is required, more seed is produced if the plants are subjected to the cold.

MN208

MN208 was derived from seed collected from a chance seedling on the #17 green of the Nassau Country Club. The seed was accessioned as family number 18.

Fifteen plants were started from seed in pots in the greenhouse and evaluated for the desired characteristics. The plant was identified as a perennial type, and seedling 18D was selected as possessing the most desired traits.

Family 18 plants exhibited a seasonal flowering habit, dark green color, low spreading habit, moderate to heavy seed production, vigorous spreading habit, and tended to produce two flushes of flowers in the spring separated by about 3–5 weeks. There is potentially some flowering in the fall, as well. Strong maternal inheritance was observed.

The selection 18D was reaccessioned as MN208 as successive generations were produced both from seed and vegetatively. As described above for MN184, MN208 was propagated asexually and planted in an experimental nursery. The seed was similarly used to establish nursery plots, from which a 2 acre seed nursery was established.

Each successive generation was evaluated for trueness to type and maintained under close supervision, and has remained stable to type. MN208 is a dark green, vigorous perennial with a vigorous spreading habit. It requires either vernalization or long days to flower and exhibits a seasonal flowering habit with two flushes of flowers in the Spring.

MN117

MN117 was derived from seed collected from a wild single plant in the rough on the Nassau Country Club (Nassau, N.Y.). The seed was accessioned as family 10, and the plant was described as having long (tall) seed heads. Fifteen plants were started from seed in pots in the greenhouse. Seedling 10C was identified as having the most desirable characteristics and was propagated through succeeding generations.

Plants derived from 10C exhibited many positive characteristics, including superior vigor, good seed production, above average density, medium stoloniferous habit, medium to coarse texture, dark green color, dense compact growth habit, large inflorescence, vigorous root habit and long, tall, seed heads and upright leaf habit.

Early observations of this family revealed a large range of vigor, however, most of the progeny exhibited superior vigor. Plant 10C was propagated by seed, as well as asexually. Plants derived from 10C were reaccessioned as MN117, and successive generations were produced.

As described above for MN184, MN117 was reproduced asexually and planted in an experimental replicated nursery. Seed from these plants was used to establish current nurseries. Each succeeding planting was evaluated for trueness to type and maintained under close supervision.

Plants exhibited a reduced flowering habit restricted to about 4–6 weeks in the spring. Flowering is induced either by exposure to cold or by short day photoperiod. When unmowed, the plants exhibit an upright, mound spreading habit of growth, with leaves in the vegetative stage (non-flowering condition) being almost upright.

MN234

MN234 was derived from a plant obtained from the University of Minnesota "Les Bolstad" Golf Course, St. Paul, Minn. As described above for MN184 and MN117, 15 seeds were planted and one plant exhibiting the most desired characteristics was selected for continued development.

Early observations indicated MN234 had very heavy seed production, low mounds with flat-spreading 2–3" tall leaves spreading 12"–14" in diameter. The plants had dark green color, vigorous spreading habit, exhibited two flushes of flower or more and produced large amounts of seed in the late Spring–early Summer. Its flowering habit is continuous, with reduced flowering in Summer and Fall.

The variety has nice dark green color, is upright, but a moderately vigorous spreader, producing mounds about 5–6 inches high with about a 10–12 inch spread when space planted. Flowering is induced by either vernalization or long day exposure. When space planted, the flowers tend to be found flat out on the soil. Rooting is observed at the nodes under the canopy.

The following Table 1 compares the characteristics of each of the novel varieties of the invention:

TABLE 1

|  | MN184 | MN42 | MN208 | MN234 | MN117 |
| --- | --- | --- | --- | --- | --- |
| Perennial Nature | Perennial | Perennial | Perennial | Perennial | Perennial |
| Disease Resistance | Pink snow mold; some dollar spot, mildew, rust | Pink snow mold, some dollar spot, mildew, rust | Pink snow mold, some dollar spot, mildew, rust | Pink snow mold, some dollar spot, mildew, rust | Pink snow mold, some dollar spot, mildew, rust |
| Mowing | ⅛" cleanly | ⅛" cleanly | ⅛" cleanly | ⅛" cleanly | ⅛" cleanly |
| Color | Dark Green | Dark Green | Dark Green | Dark Green | Dark Green |

TABLE 1-continued

|  | MN184 | MN42 | MN208 | MN234 | MN117 |
|---|---|---|---|---|---|
| Flower Habit | Seasonal Spring (2–3 weeks) | Seasonal Spring (4–6 weeks) 20 tillers | Seasonal, Spring, with 2 Fushes | Continuous, reduced in Summer and Fall | Seasonal - Spring (4–6 weeks) |
| Vernalization | Requires Cold | Permissive Cold | Permissive Cold | Permissive Cold | Permissive Cold |
| Day Length | Unaffected | Short Days | Long Days | Long Days | Short Days |
| Growth Habit | Spreading Mound | Spreading | Spreading | Spreading | Spreading Mound |
| Texture | Fine | Medium | Medium | Medium | Fine–Med. |
| Chromosome Number | 28 | 28 | 28 | 28 | 28 |

The invention will be further described by reference to the following detailed examples.

EXAMPLE 1

Seed and Seed Increase

Seedling Vigor:

In at least the following varieties of *Poa annua*, MN184, MN42, MN208, MN234, and MN117, it is observed that plantings established from seed are more vigorous and productive than plantings established from sod. This indicates that seedling vigor is an important characteristic in establishing *Poa annua*. In most cases, satisfactory plantings were established by seeding at a rate of about 1 pound of seed per thousand square feet.

Seed Dormancy and Germination:

Germination for some varieties of *Poa annua*, including MN184, MN42, MN208, MN234, and MN117, is increased by after ripening of the seeds. *Poa annua reptans* types MN184 and MN117, in particular, benefited from a pre-planting vernalization treatment. Dormancy was overcome by imbibing the seeds for 8 hours and subjecting the seeds to 4° C. for 7–10 days. In other cases, dormancy or after-ripening requirements were fulfilled by seven months at 4° C.

Seed Increase

Seed increase was typically accomplished by establishing small breeder's seed plantings. Initially, the seeding rate for seed production was at a rate of 5 lbs/acre of each of numbers MN42, MN184, MN208, and MN234 were planted. After eight months of growth, seed was harvested, dried, and processed. In this initial trial, each selection yielded only about five pounds of seed.

In turf plantings, a seeding of 1.3 pounds per thousand square feet sown in late September resulted in dense turf by late April in Minnesota.

Differences in growth habit of seed propagated compared to plants vegetatively propagated by stolons were observed in selections in spaced planting. Plants grown directly from seed spread far more vigorously than those propagated vegetatively. A rough statistical comparison indicated that the vegetatively established sod grew at only about ⅔ the rate of the seed propagated planting, when measured several weeks after transplanting to the field. This suggests that *Poa annua* competes for space effectively by establishing itself rapidly from seed. Later, vegetative reproduction leads to growth patterns related to consolidation and reproduction.

Seed increase trials were continued to investigate optimization of seed production. In a second trial, separate blocks of MN42, MN117, MN184, MN208, and MN234 were planted. There was sufficiency of these selections to allow continuation of seed increase evaluation. Seed was harvested, dried, and processed, and subjected to air separation to remove extraneous material by conventional methods. Table 2 indicates the results of seed increase for each of the varieties.

TABLE 2

Seed Yield Estimates from First Increase for Breeder's Seed at Pickseed USA, Tangent, Oregon

| Selection # | MN42 | MN117 | MN184 | MN208 | MN234* |
|---|---|---|---|---|---|
| Seed Wt (lb) | 9.02 | 9.24 | 15.27 | 14.83 | 4.90 |
| Area (sq. ft.) | 1600 | 800 | 1600 | 800 | 800 |
| Estimated yield (lb/acre) | 246 | 503 | 416 | 807 | 267 |

*The small amount of seed associated with MN234 is not indicative of the seed production potential of this selection. The reduction in yield is directly related to a mistake in preemergent herbicide application to a substantial amount of the seed production block.

Further studies of seed increase and of seed field plantings were pursued for selections MN42, MN184, and MN208. For selections MN42 and MN184, one acre was seeded; and two acres of selection MN208 were seeded. The seeding occurred on a site that had grown certified perennial rye grass for the previous four years.

Prior to the perennial rye grass, certified Penncross bent grass was grown on the site. The land had never been in bluegrass production. Planting was completed with a John Deere 450 double disk drill in 7½ foot rows that were 1,560 feet long with 1 pound of seed being sown on each acre. Two days prior to planting and 16 days after planting the plots were treated with Roundup. Germination, as determined by emergence of grass, was observed on January 15th of the following year. The herbicide Buctril and Banvel-D were applied on March 25 with no apparent damage to the Poa. The Poa started to exhibit seed heads around May 10. Despite a late planting in November, the seed crop was quite respectable.

Some of the seed was collected with a rotary mower with a grass catching attachment. The material collected by the lawnmower was spread in windrows on paper to cure. The flowering culms were mowed with a standard grass seed windrower on the 20th of June.

In the first year, *Poa annua* type MN42 yielded the most uniform heading and exhibited the least shattering. Types MN184 and MN208 exhibited some uneven ripening and some shattering.

Variety MN42 produced 291 pounds of seed. Variety MN184 produced 174 pounds of seed. Variety MN208 produced 305 pounds of seed. This experiment in seeding yielded three major conclusions:

1. These varieties of *Poa annua* can be productively planted quite late in the season (November).
2. Standard equipment and practices successfully harvest seed from *Poa annua*.
3. Each of the selections tested produced sufficient seed to warrant continued seed production, breeding, and introduction.

EXAMPLE 2

SELECTED *POA ANNUA* VARIETIES

General Procedures:

Several varieties of *Poa annua* were collected as seed from different plants on Long Island, N.Y. Approximately 15 seeds of each family were planted in a greenhouse at the University of Minnesota. Optimum conditions to support germination and growth were maintained. Seedlings were started in November and grown through the winter with a 60° nighttime temperature and a 70° daytime temperature with no supplemental light. The first selection was made according to the habit of growth. Desirable habit of growth observed included density, restricted spring flowering, required vernalization for flowering, and short stolen length compared to wild type. About 100 seeds from those plants with a desired habit of growth were selected and further propagated. Of these selections, about 18 were chosen for further propagation both sexually and asexually. The further propagation was done to increase the amount of plant matter and to acquire more seed. In addition, the uniformity of the type was evaluated as it reproduced. The plants were grown outdoors in a cold frame to induce flowering and then brought inside. Details of the flowering habit and flowering induction for *Poa annua* varieties are described above.

When sufficient amount of plant material and seed for these *Poa annua* types had been produced, several were selected on the basis of turf characteristics described above for further evaluation and reproduction.

Variety MN184

One of the selected desirable *Poa annua* types was seeded out of doors while asexual reproduction continued both indoors and in the field. Sufficient plant material was obtained to plant 2'×2' plots in a field for initial evaluation of tolerance to close mowing.

This variety tolerated mowing down to ⅛". In addition, succeeding generations were sufficiently true to type to merit further selection within this type of perennial *Poa annua*. Additional generations were grown to show that the previously observed desired habit and tolerance of mowing were sustainable throughout the generations. In each of the first five generations, off-types were eliminated. Desirable habits of growth used for selection included density, restricted spring flowering. Stolon length in unmowed grass was only about 4–5", compared to about 12"–14" in some other types.

Seed (2500) of MN184 was deposited at the American Type Culture Collection (ATCC) on Sep. 12, 1996 having accession No.: 97711.

This variety of *Poa annua* when vegetatively reproduced produced a dense mound of a type not found in the other inventive varieties of *Poa annua* described herein. This mound is produced prior to flower induction and includes leaves of a fine texture. Type MN184 is also distinguished by its flowering period after vernalization of only about 3 weeks.

*Poa annua* Type MN42

Another desirable type of *Poa annua* was also selected. Type MN42 is characterized by dense growth but more flowering culms than in type MN184. It is more vigorous than type MN184. This type is a lighter green than MN184.

Seed (2500) of MN42 was deposited at the American Type Culture Collection (ATCC) on Sep. 12, 1996 having accession No.: 97712.

*Poa annua* Type MN208

A very vigorous type of *Poa annua* was also selected from the original types. Compared to types MN184 and MN42, type MN208 produces more vegetation, grows more rapidly, and has a longer stolon. It is a continuous flowering variety but produces fewer flowers than the wild type. It does not require vernalization for flowering, but has a day length requirement.

Seed (2500) of MN208 was deposited at the American Type Culture Collection (ATCC) on Sep. 12, 1996 having accession No.: 97714.

*Poa annua* Type MN117

Seed (2500) from MN117 was deposited at the American Type Culture Collection (ATCC) on Sep. 12, 1996 having accession No.: 97713.

*Poa annua* Type MN234

Seed (2500) of MN234 was deposited at the American Type Culture Collection (ATCC) on Sep. 12, 1996 having accession No.: 97715.

EXAMPLE 3

Photoperiod and Vernalization:

Photoperiod responses were assessed by growing seedlings of the five varieties under short day (SD, 8 hour) and long days (LD, 20 hour) conditions. Results are indicated below in Table 3.

Approximately 12 weeks of vernalization are required for flower induction where vernalization is a requirement. No differences were observed between LD and SD treatments during the vernalization treatments.

TABLE 3

Summary of Photoperiod and Vernalization* Flowering Requirements of Selected Perennial *Poa annua* Genotypes

| Genotype | Requirements |
| --- | --- |
| MN42 | Short days (SD) induce flowering; but vernalization appears to hasten or otherwise enhance floral induction |
| MN117 | Short-days (SD) induce flowering; Vernalization enhances induction. Flowering is inhibited by long-days (LD) |
| MN184 | Vernalization is required for floral induction |
| MN234 | Long Days required for induction. Vernalization enhances induction. |
| 2283** | Day-neutral; no vernalization affects |

*Vernalization conditions are 3–5 C. Short Day - an 7 hour photoperiod. Long day - 8 hour day + a 2 hour incandescent night light break.
**2283 is a control, annual, continuous flowering wild type

EXAMPLE 4

Comparison of New Cultivars with Wild-Type *Poa annua*

Measurements of the stolons, internodes, leaves, panicle and branches were made on plants from each of the new cultivars of *Poa annua* and on wild-type *Poa annua* plants. A first wild-type was obtained from a field in Tangent, Oreg., and was green-house grown in Minnesota in pots. A second wild-type was measured in a field at the University of Minnesota, the field mowed at about two inches. These were well established volunteer plants at the edge of an irrigated mixed turf area, mowed to about two inches approximately twice per week. Measurements of the new cultivars were made on plants that were grown in the field under seed production conditions, unmowed.

TABLE 4

|  | Oregon* Wild-Type (n = 15) | UMN Wild** Field Types (n = 15) | MN184 (n = 20) | MN117 (n = 4) | MN208 (n = 7) | MN234 (n = 4) | MN42 (n = 7) |
|---|---|---|---|---|---|---|---|
| Stolon Length (cm) | na | na | 36.65 | 39.75 | 36.14 | 37.5 | 27.0 |
| Internode Width (mm) | na | na | 1.2 | 1 | 1.0 | 1 | 1.0 |
| Internode Length (mm) | na | na | 90.8 | 92 | 63.71 | 76.75 | 50.29 |
| Subtending leaf length (cm) | 7.33 | 2.85 | 4.45 | 5.25 | 4.86 | 4.5 | 3.14 |
| Subtending leaf width (mm) | 3.80 | 1.46 | 1.9 | 2 | 1.43 | 1.75 | 1.29 |
| Flag Leaf Length (cm) | 5.20 | 1.92 | 2.55 | 2.5 | 2.86 | 2 | 1.43 |
| Flag Leaf Width (mm) | 2.60 | 1.0 | 1.3 | 1.25 | 1.14 | 1.25 | 1.0 |
| Panicle, Whorl to Top (cm) | 6.87 | 2.85 | 4.7 | 5 | 4.43 | 4 | 4.29 |
| Panicle, Flag to Top (cm) | 10.53 | 5.77 | 12.1 | 13.25 | 11.86 | 9.75 | 9.57 |
| # Branches-Lowest Whorl | 1.87 | 1.38 | 1.7 | 1.5 | 1.57 | 1.75 | 2.0 |

*Greenhouse grown
**Mowed at 2"

The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A perennial cultivar of *Poa annua* that is uniform and stable to type, wherein said cultivar has a restrictive flowering habit.

2. The perennial cultivar of *Poa annua* of claim 1, wherein the restrictive flowering habit comprises flowering predominantly in the spring.

3. The perennial cultivar of *Poa annua* of claim 2, wherein the restrictive flowering habit comprises flowering for about 2–3 weeks.

4. The perennial cultivar of *Poa annua* of claim 2, wherein the restrictive flowering habit comprises flowering for about 4–6 weeks.

5. The perennial cultivar of *Poa annua* of claim 2, wherein the flowering comprises two flushes of flowers.

6. The perennial cultivar of *Poa annua* of claim 5, wherein the two flushes of flowers are separated by about 3–5 weeks.

7. The perennial cultivar of *Poa annua* of claim 1, wherein the restrictive flowering habit comprises reduced flowering in the summer.

8. The perennial cultivar of *Poa annua* of claim 1, wherein the restrictive flowering habit comprises producing secondary flowering tillers.

9. The perennial cultivar of *Poa annua* of claim 1, wherein flowering is induced by exposure to cold, short day length, or long day length.

10. The perennial cultivar of *Poa annua* of claim 1, wherein flowering is unaffected by day length.

11. The perennial cultivar of *Poa annua* of claim 1, wherein the flowering exhibits a faculative vernalization.

12. The perennial cultivar of *Poa annua* of claim 1, wherein the variety produces a greater amount of seed when plants are subjected to cold.

13. The perennial cultivar of *Poa annua* of claim 1, wherein a plant of the cultivar produces up to about 5 secondary flowering tillers during the flower development period.

14. The perennial cultivar of *Poa annua* of claim 1 having a dense growth habit.

15. The perennial cultivar of *Poa annua* of claim 14, wherein the dense growth habit comprises, in the unmowed state, a vigorous, low, and dense spreading growth.

16. The perennial cultivar of *Poa annua* of claim 14, wherein the dense growth habit comprises, in the unmowed state, low spreading stolons with multiple tillers per stolon during flower production.

17. The perennial cultivar of *Poa annua* of claim 14, wherein the dense growth habit comprises, in the unmowed state, a dense but decumbent growth habit.

18. The perennial cultivar of *Poa annua* of claim 14, wherein the growth habit comprises, in the unmowed state, a tightly packed, dense, spreading mound.

19. The perennial cultivar of *Poa annua* of claim 14, wherein the growth habit comprises, in the unmowed state, a tightly packed, dense, spreading mound, which when left unmowed takes on a conical shape.

20. A perennial cultivar of *Poa annua* that is stable to type having the identifying characteristics of MN184 (A.T.C.C. No.97711), MN117 (A.T.C.C. No.97713), MN208 (A.T.C.C. No.97714), MN234 (A.T.C.C. No.97715), and MN42 (A.T.C.C. No.97712).

21. A *Poa annua* cultivar having all of the physiological and morphological characteristics of any of the *Poa annua* cultivars of claim 20.

22. Plant tissue produced by the perennial *Poa annua* of claim 1.

23. Seed produced by the perennial *Poa annua* of claim 1.

24. An ovule of the perennial *Poa annua* of claim 1.

25. An isolated plant of the perennial *Poa annua* of claim 1.

26. A *Poa annua* cultivar produced either from seed or vegetatively from the perennial *Poa annua* of claim 1.

27. The perennial *Poa annua* cultivar according to claim 1, wherein the variety withstands mowing to about ⅛".

28. A perennial *Poa annua* cultivar that is stable to type and withstands mowing to about ⅛", that flowers after vernalization for about 3 weeks or less, and that produces, when grown in a pot, a dense mound of finely textured plant material.

29. Seed producing a *Poa annua* cultivar that is stable to type having the identifying characteristics of MN184

(A.T.C.C. No. 97711), MN208 (A.T.C.C. No. 97713), MN234 (A.T.C.C. No. 97714), or MN42 (A.T.C.C. No. 97712).

30. A turf comprising a perennial cultivar of *Poa annua* that is stable to type, wherein said cultivar has a restrictive flowering habit.

31. A sports field turf, lawn turf, or park turf comprising a perennial cultivar of *Poa annua* that is stable to type, wherein said cultivar has a restrictive flowering habit.

32. The sports field turf of claim 31, useful for playing golf.

33. The sports field turf of claim 31, wherein the cultivar of *Poa annua* has a restrictive flowering habit.

34. The sports field turf of claim 33, wherein the restrictive flowering habit comprises flowering predominantly in the Spring.

35. The sports field turf of claim 33, wherein the restrictive flowering habit comprises reduced flowering in the Summer.

36. The sports field turf of claim 31, wherein the cultivar of *Poa annua* is induced to flower by exposure to cold, short day length, or long day length.

37. The sports field turf of claim 31, wherein flowering is unaffected by day length.

38. The sports field turf of claim 31, wherein the cultivar of *Poa annua* has a dense growth habit in the unmowed state.

39. The sports field turf of claim 38, wherein the dense growth habit comprises a tightly packed, upright but spreading mound.

40. The sports field turf of claim 38, wherein the perennial cultivar has the identifying characteristics of MN184 (A.T.C.C. No.97711), MN117 (A.T.C.C. No.97713), MN208 (A.T.C.C. No.97714), MN234 (A.T.C.C. No.97715), or MN42 (A.T.C.C. No. 97712).

41. The sports field turf of claim 40, wherein the perennial cultivar is MN184 (A.T.C.C. No. 97711).

* * * * *